US012337115B1

(12) United States Patent
Geraghty

(10) Patent No.: US 12,337,115 B1
(45) Date of Patent: *Jun. 24, 2025

(54) ENDOTRACHEAL TUBE APPARATUS

(71) Applicant: MONITORING FOR LIFE, LLC, Londonderry, NH (US)

(72) Inventor: Scott P. Geraghty, Londonderry, NH (US)

(73) Assignee: MONITORING FOR LIFE, INC., Wilmington, DE (US)

( * ) Notice: Subject to any disclaimer, the term of this patent is extended or adjusted under 35 U.S.C. 154(b) by 1124 days.

This patent is subject to a terminal disclaimer.

(21) Appl. No.: 16/021,943

(22) Filed: Jun. 28, 2018

Related U.S. Application Data

(63) Continuation of application No. 14/209,706, filed on Mar. 13, 2014, now Pat. No. 10,010,690.

(Continued)

(51) Int. Cl.
*A61M 16/08* (2006.01)
*A61B 1/00* (2006.01)
(Continued)

(52) U.S. Cl.
CPC ....... *A61M 16/085* (2014.02); *A61B 1/00124* (2013.01); *A61B 1/0676* (2013.01); *A61B 1/0684* (2013.01); *A61B 5/0836* (2013.01); *A61B 5/097* (2013.01); *A61M 16/0434* (2013.01); *A61M 16/0463* (2013.01);
(Continued)

(58) Field of Classification Search
CPC .............. A61M 16/0402; A61M 16/04; A61M 2205/587; A61M 2205/8206; A61B 1/0676; A61B 1/0684; A61B 1/0661
See application file for complete search history.

(56) References Cited

U.S. PATENT DOCUMENTS 2,797,683 A  7/1957  Aiken
4,334,534 A  6/1982  Ozaki
(Continued)

FOREIGN PATENT DOCUMENTS

WO   2014004762   1/2014

OTHER PUBLICATIONS

Office Action dated Feb. 24, 2021, issued in U.S. Appl. No. 16/173,739, 28 pages.
(Continued)

*Primary Examiner* — Thaddeus B Cox
*Assistant Examiner* — Karen E Toth
(74) *Attorney, Agent, or Firm* — Grossman, Tucker, Perreault & Pfleger, PLLC; Michael J. Gallagher

(57) ABSTRACT

An endotracheal tube apparatus is provided which comprises an endotracheal tube insertable into a trachea of a patient, wherein the endotracheal tube has a sidewall and includes a first passageway, wherein the first passageway is a ventilation passageway to provide ventilation to the patient; a fluid sampling port connected to the sidewall of the endotracheal tube; the fluid sampling port including a fluid sampling passageway, the fluid sampling passageway to obtain a fluid sample comprising one or more gases exhaled from the patient; and the fluid sampling port including a connector to connect the fluid sampling port to an analyzer to detect a presence of carbon dioxide gas in the fluid sample.

22 Claims, 11 Drawing Sheets

Related U.S. Application Data

(60) Provisional application No. 61/790,738, filed on Mar. 15, 2013.

(51) Int. Cl.
*A61B 1/06* (2006.01)
*A61B 5/083* (2006.01)
*A61B 5/097* (2006.01)
*A61M 16/04* (2006.01)
*A61M 16/10* (2006.01)

(52) U.S. Cl.
CPC .... *A61M 16/0484* (2014.02); *A61M 16/0486* (2014.02); *A61M 16/105* (2013.01); *A61M 2016/0413* (2013.01)

(56) References Cited

U.S. PATENT DOCUMENTS

| | | | |
|---|---|---|---|
| 4,488,548 A | 12/1984 | Agdanowski | |
| 4,567,882 A | 2/1986 | Heller | |
| 4,669,463 A | 6/1987 | McConnell | |
| 4,834,087 A | 5/1989 | Coleman et al. | |
| 4,850,371 A | 7/1989 | Broadhurst et al. | |
| 5,193,544 A | 3/1993 | Jaffe | |
| 5,357,946 A | 10/1994 | Kee et al. | |
| 5,421,821 A | 6/1995 | Janicki et al. | |
| 5,657,750 A | 8/1997 | Colman et al. | |
| 5,855,203 A | 1/1999 | Matter | |
| 5,857,461 A | 1/1999 | Levitsky et al. | |
| 6,422,240 B1 | 7/2002 | Levitsky et al. | |
| 6,437,316 B1 | 8/2002 | Colman et al. | |
| 6,843,769 B1 | 1/2005 | Gandarias | |
| 6,926,005 B1 | 8/2005 | Colman et al. | |
| 7,503,328 B2 | 3/2009 | Kolobow et al. | |
| 8,074,649 B2 | 12/2011 | Dhuper et al. | |
| 8,323,207 B2 | 12/2012 | Popov et al. | |
| 10,010,690 B1 | 7/2018 | Geraghty | |
| 10,112,024 B2 | 10/2018 | Geraghty et al. | |
| 2003/0078476 A1 | 4/2003 | Hill | |
| 2003/0199807 A1 | 10/2003 | Dent et al. | |
| 2004/0120156 A1 | 6/2004 | Ryan | |
| 2004/0138531 A1 | 7/2004 | Bonner et al. | |
| 2004/0210114 A1* | 10/2004 | Simon | A61M 16/0484 600/185 |
| 2004/0215061 A1 | 10/2004 | Kimmel et al. | |
| 2005/0039754 A1* | 2/2005 | Simon | A61B 1/0676 128/207.14 |
| 2005/0279354 A1* | 12/2005 | Deutsch | A61M 16/0463 128/200.24 |
| 2007/0088317 A1 | 4/2007 | Hyde | |
| 2007/0129603 A1* | 6/2007 | Hirsh | A61B 1/00108 600/179 |
| 2007/0221229 A1 | 9/2007 | Rahaghi et al. | |
| 2007/0277828 A1 | 12/2007 | Ho et al. | |
| 2010/0137732 A1 | 6/2010 | Haveri | |
| 2010/0168599 A1 | 7/2010 | Esposito et al. | |
| 2010/0229863 A1 | 9/2010 | Euk | |
| 2010/0249639 A1 | 9/2010 | Bhatt | |
| 2010/0280362 A1 | 11/2010 | Li et al. | |
| 2011/0178419 A1 | 7/2011 | Wood et al. | |
| 2011/0300505 A1 | 12/2011 | Jessop et al. | |
| 2012/0002427 A1 | 1/2012 | Moon et al. | |
| 2012/0101343 A1 | 4/2012 | Duffy et al. | |
| 2012/0172664 A1 | 7/2012 | Hayman et al. | |
| 2012/0321509 A1 | 12/2012 | Bak | |
| 2013/0053636 A1 | 2/2013 | Hayman et al. | |
| 2013/0092171 A1 | 4/2013 | Sederstrom et al. | |
| 2013/0303849 A1 | 11/2013 | Allyn et al. | |
| 2014/0180252 A1 | 6/2014 | Gabriel | |
| 2015/0190649 A1 | 7/2015 | Gelfand et al. | |
| 2016/0296719 A1 | 10/2016 | Geraghty et al. | |

OTHER PUBLICATIONS

International Search Report and Written Opinion dated May 6, 2015, issued in PCT Patent Application No. PCT/US2015/011818, p pages.

International Preliminary Report on Patentability dated Jul. 28, 2016, issued in PCT Patent Application No. PCT/US2015/011818, 7 pages.

U.S. Office Action dated Aug. 2, 2016, issued in U.S. Appl. No. 14/209,706, 11 pages.

International Search Report and Written Opinion dated Jul. 26, 2016, issued in PCT Patent Application No. PCT/US2016/028949, 10 pages.

Office Action dated Nov. 2, 2016, issued in U.S. Appl. No. 15/136,587, 17 pages.

Office Action mailed Dec. 19, 2017, issued in U.S. Appl. No. 15/136,587, 29 pages.

\* cited by examiner

ENDOTRACHEAL TUBE APPARATUS

CROSS-REFERENCE TO RELATED APPLICATIONS

This application is a continuation of U.S. patent application Ser. No. 14/209,706 filed Mar. 13, 2014 which claims the benefit of U.S. Provisional Patent Application Ser. No. 61/790,738, filed Mar. 15, 2013, the entire disclosure of each being incorporated herein by reference.

FIELD

This disclosure relates generally to the field of medical devices, and more specifically to an endotracheal tube apparatus to be used on a human body.

BACKGROUND

Artificial respiration involves assisting or stimulating a person's natural respiration, a metabolic process referring to an exchange of gases within the body by pulmonary ventilation, external respiration and internal respiration. Pulmonary ventilation is achieved through manual insufflation of a person's lungs by causing air or oxygen to flow in and out of a person's lungs, generally when natural breathing has stopped or is otherwise inadequate.

One method of pulmonary ventilation involves intubation, or entubation, which pertains to the insertion of a tube generally into an external orifice of the body. Once particular method of intubation is tracheal intubation, in which a flexible plastic tube is inserted into the trachea (windpipe) of a person to provide or maintain an open airway, or to serve as a conduit through which to administer certain drugs. Tracheal intubation is often performed in critically injured or anesthetized patients to facilitate pulmonary ventilation and to prevent the possibility of asphyxiation or airway obstruction. Tracheal intubation is most often orotracheal, or endotracheal, in which an endotracheal tube is passed through the mouth and vocal apparatus of a person and into the trachea.

During an endotracheal intubation, the person's mouth is opened and the endotracheal tube is inserted down the throat. To better ensure the endotracheal tube is properly positioned, a laryngoscope may be used to bring the vocal cords and larynx into view prior to inserting the endotracheal tube. The tube may then inserted in the trachea through the vocal cords to the point that an inflation cuff surrounding a distal end portion of the tube rests just below the vocal cords. Finally, after an inflation cuff is inflated to inhibit leakage, a bag valve mask is squeezed at a proximal end of the tube to pass air and/or oxygen to the lungs. A stethoscope may then be used by medical personnel to listen for breathing sounds to ensure proper placement of the tube.

Often endotracheal intubation must be performed away from a clinic and in the field, particularly during a trauma and other emergency situations. Unfortunately, under such adverse conditions, it may not be possible to use a laryngoscope or a stethoscope to ensure proper placement of the endotracheal tube in the trachea, in which case the endotracheal tube may enter the esophagus.

In order to better ensure proper placement of the endotracheal tube in the trachea, a carbon dioxide sensor may be added to an adapter located at the proximal end of the endotracheal tube. However, because the carbon dioxide sensor is a separate component, use of the sensor may be overlooked. Furthermore, since the sensor is located at the proximal end of the endotracheal tube, the carbon dioxide measurements may not be particularly accurate. What is needed is an endotracheal tube to better ensure proper placement in the trachea during endotracheal intubation, as well as incorporate a carbon dioxide sensor which better ensures the sensor will be present, provides better placement for obtaining breathing samples from the lungs and addresses other needs in the art.

SUMMARY

An endotracheal tube apparatus is provided which comprises an endotracheal tube insertable into a trachea of a patient, wherein the endotracheal tube has a sidewall and includes a first passageway, wherein the first passageway is a ventilation passageway to provide ventilation to the patient; a fluid sampling port connected to the sidewall of the endotracheal tube; the fluid sampling port including a fluid sampling passageway, the fluid sampling passageway to obtain a fluid sample comprising one or more gases exhaled from the patient; and the fluid sampling port including a connector to connect the fluid sampling port to an analyzer to detect a presence of carbon dioxide gas in the fluid sample.

FIGURES

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
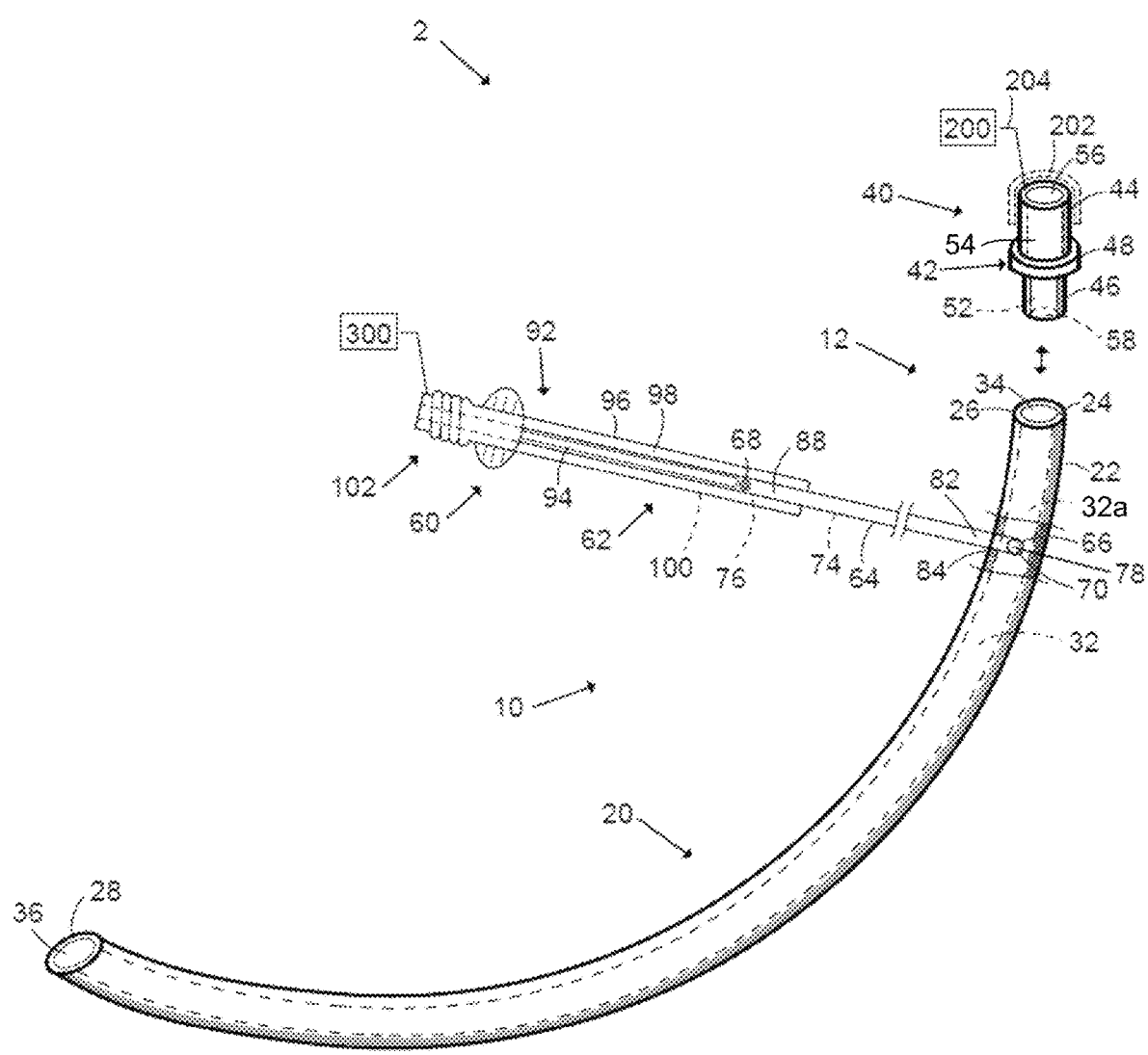
FIG. 1 shows a first embodiment of an endotracheal tube apparatus according to the present disclosure.

It may be appreciated that the present disclosure is not limited in its application to the details of construction and the arrangement of components set forth in the following description or illustrated in the drawings. The invention(s)

herein may be capable of other embodiments and of being practiced or being carried out in various ways. Also, it may be appreciated that the phraseology and terminology used herein is for the purpose of description and should not be regarded as limiting as such may be understood by one of skill in the art. Furthermore, throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive.

Referring now to FIG. 1, there is shown an endotracheal tube apparatus 10 of a respiratory system 2 according to the present disclosure. The endotracheal tube apparatus 10 comprises an endotracheal tube unit 12 and a fluid sampling port 60, explained in greater detail below.

Endotracheal tube unit 12 comprises a flexible, elongated, hollow tubular endotracheal member 20 in the form of a cylindrical, circular endotracheal tube 22 (e.g. extruded tubing) to be inserted into a trachea of a patient. Endotracheal tube 22 comprises a cylindrical sidewall 24 which defines a proximal end 26 of the tube 22, and a distal end 28 of the tube 22 as well as the apparatus 10. Sidewall 24 also defines a first (main) centrally disposed inner fluid (air) passageway 32 in the form of a lumen, as well as proximal end opening 34 and distal end opening 36 of the passageway 32. Passageway 32 may be understood as the primary passageway for tracheal intubation and subsequent use of a bag valve mask or a mechanical ventilator connected to endotracheal tube apparatus 10 to provide mechanical ventilation/respiration to the patient (i.e. a ventilation passageway).

In certain embodiments, endotracheal tube apparatus 10 may comprise an adapter fitting 40. As shown in FIG. 1, the proximal end 26 of the tube 22 includes an adapter fitting 40 that operatively connects the apparatus 10 to respirator means 200. The adapter fitting 40 comprises a cylindrical body 42 having a proximal cylindrical portion 44 and a distal cylindrical portion 46 separated by an intermediate cylindrical portion 48. Adapter 40 further comprises a ventilation passageway 52 which is defined by the sidewall 54 and extends through the proximal cylindrical portion 44, intermediate cylindrical portion 48 and distal cylindrical portion 46. Sidewall 54 also defines proximal end opening 56 and distal end opening 58 of the passageway 52. Passageway 52 is to provide fluid communication between passageway 32 of tube 22 and respirator means 200.

As shown, an outside diameter of the intermediate cylindrical portion 48 is larger than an outside diameter of the proximal cylindrical portion 44, which is larger than an outside diameter of the distal cylindrical portion 46.

The outside diameter of the distal cylindrical portion 46 of the adapter fitting 40 is dimensioned to be inserted into the passageway 32 of the tube 22 and interference (frictionally) fit with the inside diameter of the sidewall 24 thereof and contact against intermediate portion 48, which provides an annular lip.

Similarly, the outside diameter of the proximal cylindrical portion 44 of the adapter fitting 40 is dimension to by inserted into a passageway 202 of a respirator tube 204 (shown in phantom) of respirator means 200 and interference (frictionally) fit with the inside diameter of the sidewall 204 thereof and contact against intermediate portion 48.

Endotracheal tube apparatus 10 further comprises a fluid sampling port 60 connected to sidewall 24 of endotracheal tube 22. As shown in FIG. 1, fluid (exhaled gas(es) from the patient) sampling port 60 includes an elongated, hollow, tubular fluid sampling member 62 comprising a cylindrical, circular fluid sampling tube 64 (e.g. extruded tubing), having a cylindrical sidewall 66 which defines a proximal end 68 of the tube 64, and a distal end 70 of the tube 64. Sidewall 66 also defines a centrally disposed inner fluid sampling passageway 74 in the form of a lumen, as well as proximal end opening 76 and distal end opening 78 of the passageway 74.

As shown, a distal end portion 82 of the fluid sampling tube 64 and tubular fluid sampling member 62 may be joined with the tubular endotracheal member 20 such that the fluid sampling passageway 74 of the tubular fluid sampling member 62 is in fluid communication with the fluid passageway 32 of the tubular endotracheal member 20. More particularly, as shown, distal end portion 82 of the fluid sampling tube 64 may be inserted into an aperture 84 formed through the sidewall 24 of endotracheal tube 22 such that the distal end opening 78 of the fluid sampling tube 64 extends through and is located within a proximal end portion 32a of the passageway 32 of the endotracheal tube 22 (e.g. within 75 mm from the proximal end 26 and, in certain embodiments within 35 mm from the proximal end 26). Once the distal end portion 82 of the fluid sampling tube 64 is inserted into an aperture 84 formed in the sidewall 24 of endotracheal tube 22, a fluid tight seal may be formed there between by welding the fluid sampling tube 64 and the endotracheal tube 22 together at the junction thereof.

A proximal end portion 88 of the fluid sampling tube 64 may be joined to a filter means 92. Filter means 92 may comprise a filter 94 located within a filter housing 96. Filter housing 96 may comprise a fluid sampling tube 98.

As shown, an outside diameter of the proximal end portion 88 of the fluid sampling tube 64 may be dimensioned to be inserted into the lumen 100 of fluid sampling tube 98. Furthermore, the filter 94 may also be located in lumen 100 of fluid sampling tube 98. The proximal end of fluid sampling tube 98 may be joined to a threaded rigid connector 102 which connects sampling port 60 to an analyzing/monitoring apparatus 300. More particularly, sampling port 60 may be a carbon dioxide sampling port, and analyzing/monitoring apparatus 300 may be a carbon dioxide analyzer/monitor (e.g. a capnograph). Filter 94 may be particularly suited to separate liquids (e.g. saliva) from the gases (e.g. carbon dioxide) exhaled by the patient, such that the gases therein may be analyzed by a gas analyzer, such as a capnograph, which may detect a presence of carbon dioxide therein.

Figure 2:
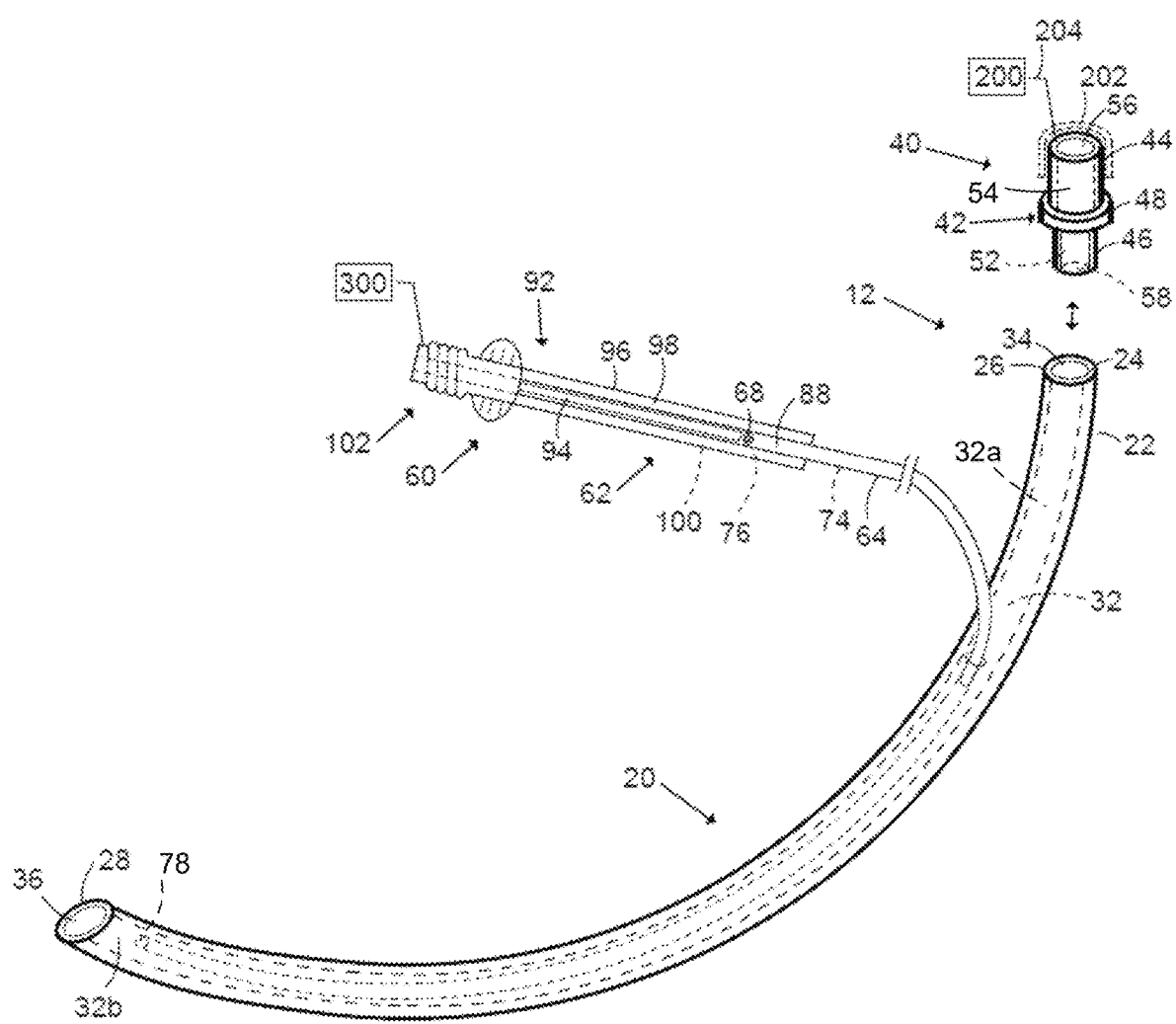
FIG. 2 shows another embodiment of an endotracheal tube apparatus according to the present disclosure.

In another embodiment of the discloser, as shown in FIG. 2, rather than sampling tube 64 terminating within a proximal end portion 32a of passageway 32, sampling tube 64 may continue distally within lumen 32 and terminate within a distal end portion 32b of passageway 32 (e.g. within 25 mm from the distal end 28 and, in certain embodiments within 10 mm from the distal end 28). In the foregoing manner, the sampling tube 64 may be closer positioned to obtain a carbon dioxide sample from the patient.

Figure 3B:
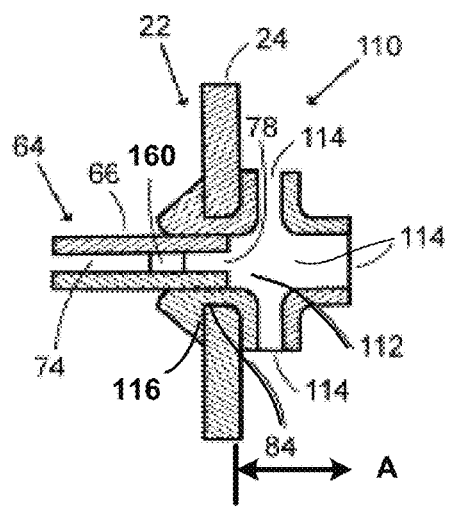
FIG. 3B is close up sectional view of the section of FIG. 3A encompassed by circle 3B.
Figure 3A:
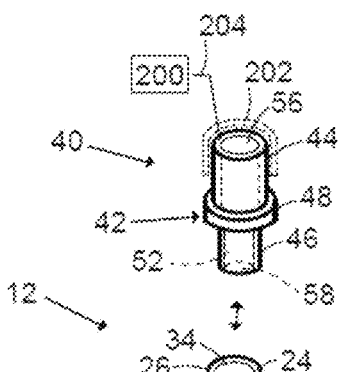
FIG. 3A shows another embodiment of an endotracheal tube apparatus according to the present disclosure.
Figure 3A:
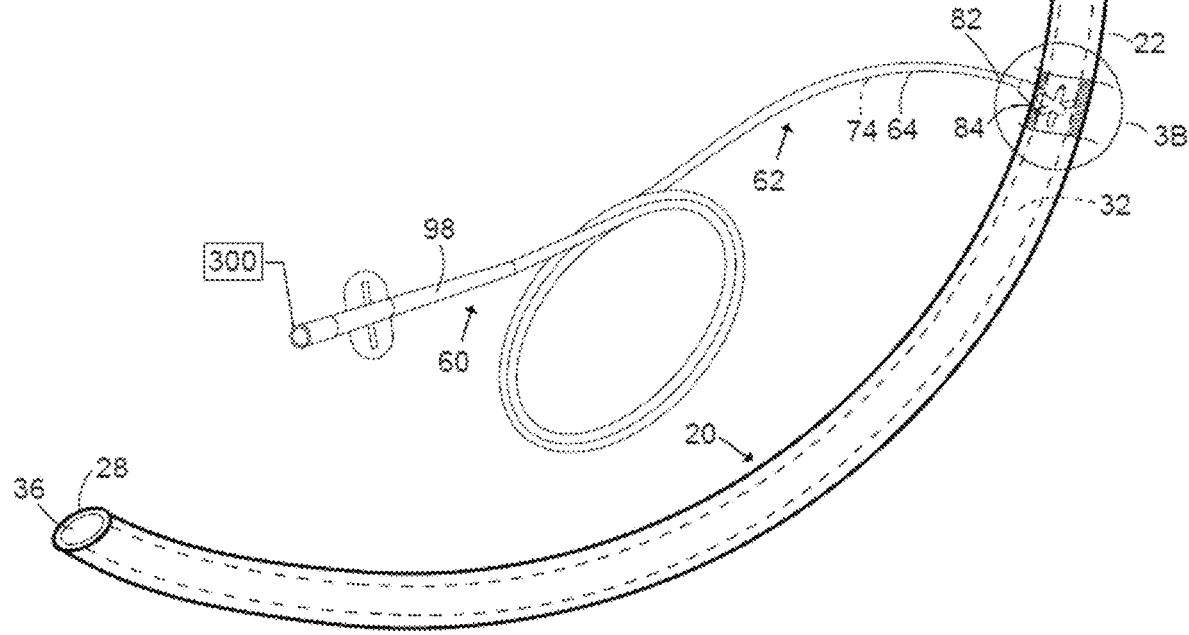

In another embodiment of the present disclosure, as shown in FIGS. 3A and 3B, a fluid sampling fitting 110 may inserted into the aperture 84 formed in the sidewall 24 of endotracheal tube 22 and a fluid tight seal may be formed there between by welding the sampling fitting 110 and the endotracheal tube 22 together at the junction thereof. Sampling fitting 66 may include a fluid passageway 112 in fluid communication with a plurality of fluid inlet openings 114, as well as fluid sampling passageway 74 of sampling tube 64 to pass fluid (e.g. carbon dioxide) there between. As compared to the first embodiment, use of a plurality of fluid inlet openings 114 may better aid in obtaining a carbon dioxide sample from the patient, and may continue to operate in the event one of the fluid inlet openings 114 becomes irreversibly clogged. In certain embodiments, the portion of fluid sampling fitting 110 within fluid passageway 32 should extend into the passageway 32 less than or equal to 5 mm as shown by arrow A, and more particularly less than or equal to 2 mm. As shown, sidewall 24 of tube 22 may be captured in a U-shaped circular undercut 116 formed by fluid sampling fitting 110.

Figure 4:
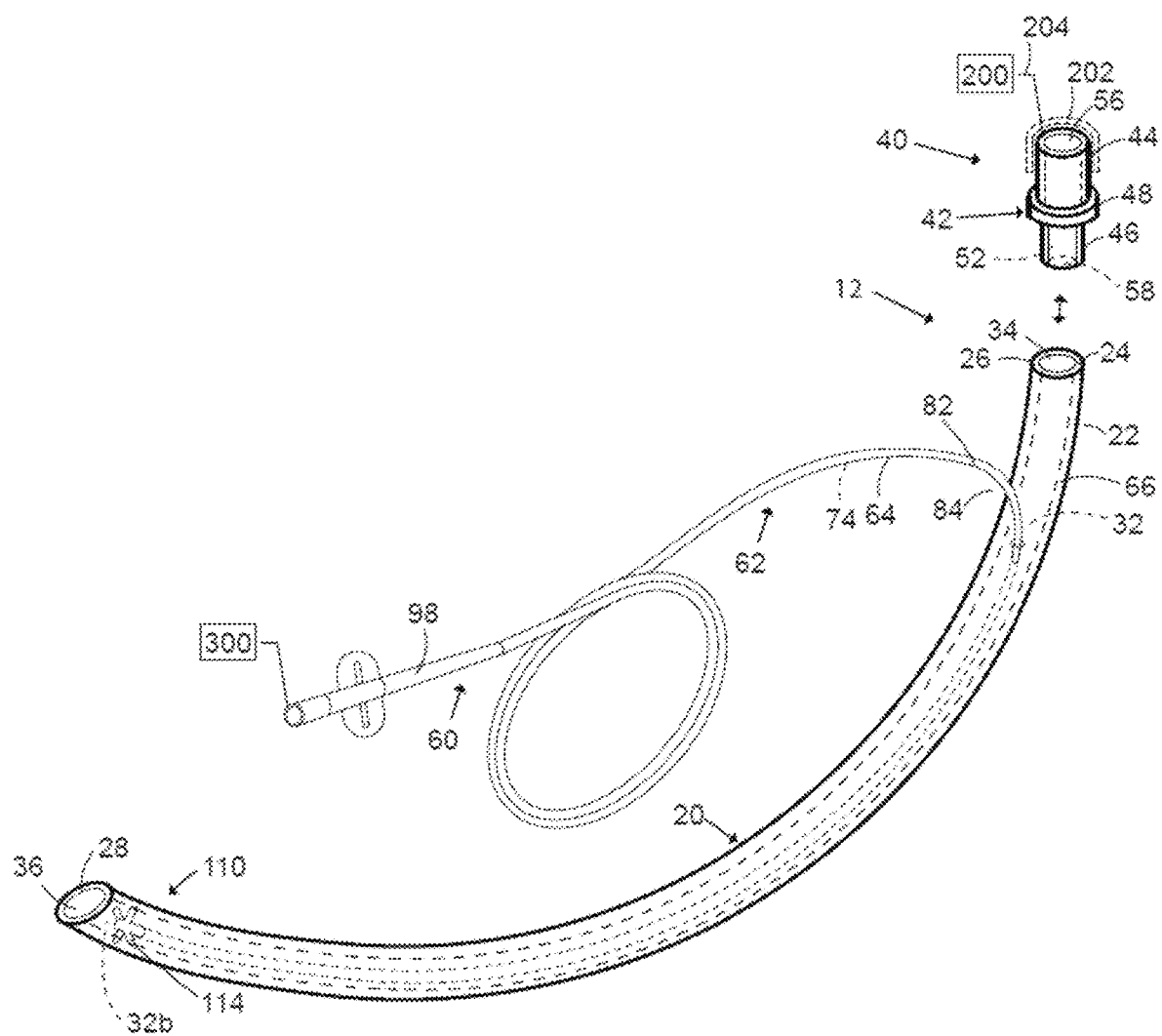
FIG. 4 shows another embodiment of an endotracheal tube apparatus according to the present disclosure.

In another embodiment of the present disclosure, as shown in FIG. 4, sampling tube 64 may continue distally within fluid passageway 32 and terminate within a distal end portion 32*b* of fluid passageway 32 with sampling fitting 110 attached thereto. In the foregoing manner, the sampling tube 64 may be closer positioned to obtain a carbon dioxide sample from the patient.

Figure 5A:
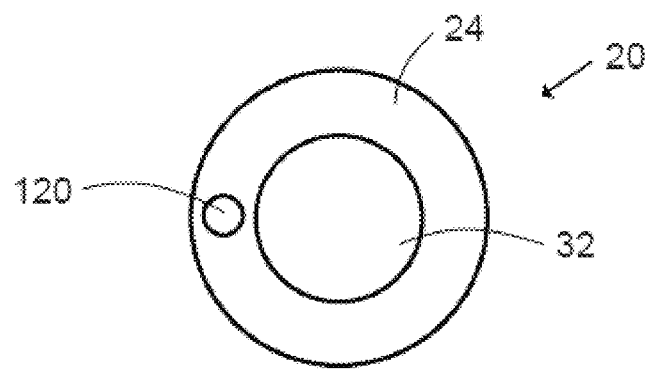
FIGS. 5A and 5B show close-up sectional views of a distal end portion of another embodiment of an endotracheal tube apparatus according to the present disclosure.
Figure 5B:
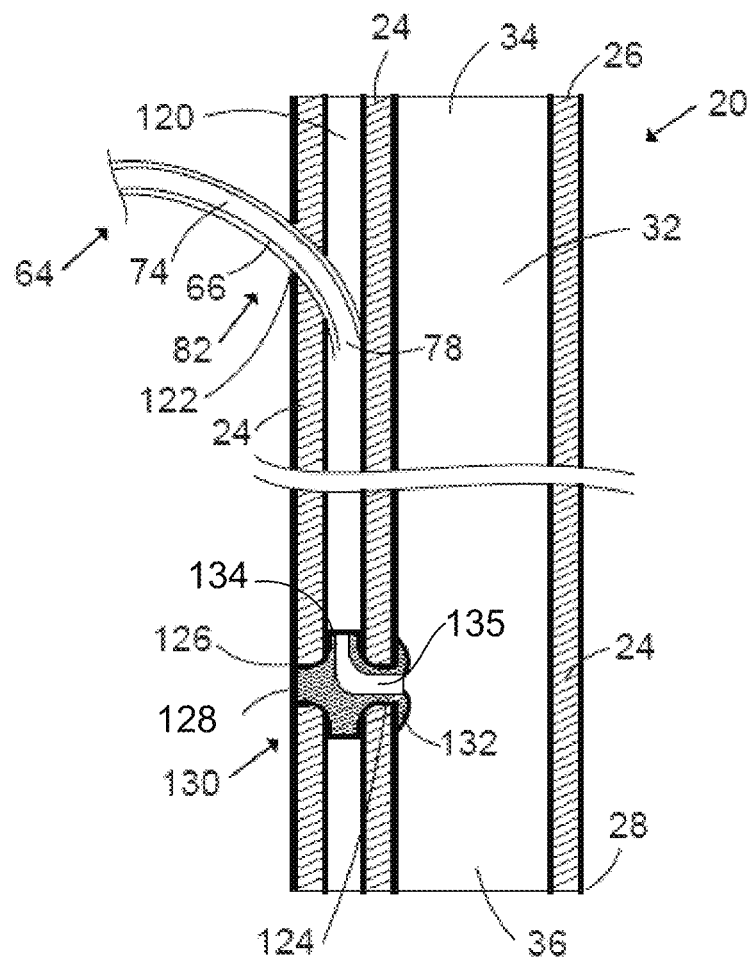

In another embodiment of the present disclosure, as shown in FIG. 5A and FIG. 5B, in addition to first fluid passageway 32 formed by the sidewall 24 of endotracheal tube 22, the endotracheal tube 22 may include a second fluid passageway 120 (co-extruded) in the form of a lumen formed in the sidewall 24 of endotracheal tube 22. As shown, the second passageway 120 is radially off-set from the first passageway 32 and extends substantially parallel (e.g. within a few degrees) along the axial length of endotracheal tube 22, similar to first fluid passageway 32.

As shown in FIG. 5B, rather than distal end portion 82 and distal end opening 78 of fluid sampling tube 64 passing completely through sidewall 24 as to be inserted into and in fluid communication with fluid (ventilation) passageway 32, the distal end portion 82 of fluid sampling tube 64 may only pass through a portion of sidewall 24 and be inserted into and in fluid communication with second passageway 120, such as by a splice connection. More particularly, as shown, distal end portion 82 of the fluid sampling tube 64 may be inserted into an aperture 122 formed in the sidewall 24 of endotracheal tube 22 such that the distal end opening 78 of the fluid sampling tube 64 is located within the second passageway 120 of the endotracheal tube 22. Once the distal end portion 82 of the fluid sampling tube 64 is inserted into an aperture 122 formed in the sidewall 24 of endotracheal tube 22, a fluid tight seal may be formed there between by welding the fluid sampling tube 64 and the endotracheal tube 22 together at the junction thereof.

As can best be seen by reference to FIG. 5B, a distal end portion of the sidewall 24 may include a circular aperture 124 (e.g. within 25 mm from the distal end 28 and, in certain embodiments within 10 mm from the distal end 28) which extends through an intermediate portion of side-wall 24 which defines both first fluid passageway 32 and second fluid passageway 120. In this manner, second fluid passageway 120 may be placed into fluid communication with first fluid passageway 132 within endotracheal tube 22. As shown, aperture 124 is formed transverse (perpendicular) to the longitudinal direction of endotracheal tube 22, as well as fluid passageway 32 and fluid passageway 120.

Sampling fitting 130 may then be inserted into aperture 124 and second fluid passageway 120. As shown, sampling fitting 130 comprises a first cylindrical portion 132 which is configured to fit within circular aperture 124, and be welded at 128 in aperture 126 flush with the outside of tube 22. Sampling fitting 130 also includes a second cylindrical portion 134 transverse to first cylindrical portion 132, which is configured to fit in fluid passageway 120. As shown, sampling fitting 130 is also held within aperture 124 and fluid passage 120 by a mechanical interference formed by the transverse cylindrical portions 132, 134 which inhibits the fitting 130 from being removed from aperture 124 and falling into either first fluid passageway 32 or second fluid passageway 120, or otherwise being removed from endotracheal tube 22.

As shown in FIG. 5B, a portion of the fluid sampling port 60 is now defined by the second passageway 120, and an L-shaped fluid passage 135 provides fluid communication between first passageway 32 and second passageway 120. In the present embodiment, the fluid sampling fitting 130 completely occludes the distal end portion of the second passageway 120. In other embodiments, fitting 130 may be eliminated, provided second passageway 120 may be provided at a suitable diameter. In still other embodiments, aperture 124 may be eliminated and the inlet to second passageway 120 may be located at the distal end 28 of the tube 22.

Figure 6:
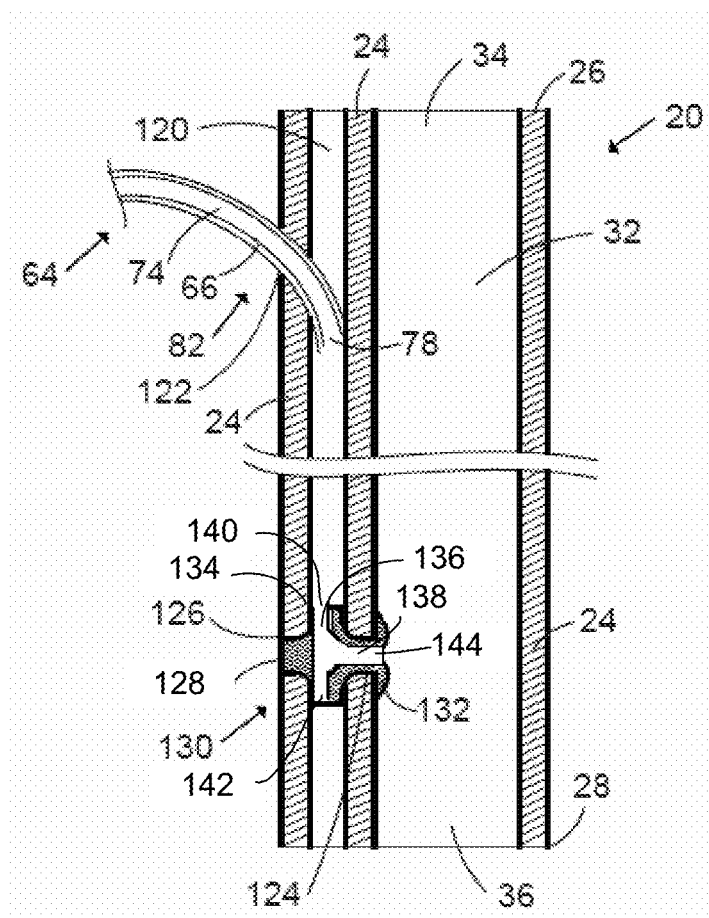
FIG. 6 shows a close-up sectional view of a distal end portion of another embodiment of an endotracheal tube apparatus according to the present disclosure.

In another embodiment of the present disclosure, as shown in FIG. 6, each cylindrical portion includes a fluid passageway 136, 138 which intersect to form a T-shape. As shown, fluid passageway 136 extends completely through second cylindrical portion 132 and is open to fluid flow from proximal opening 140 to distal opening 142 in fluid passageway 120. Fluid passageway 138 extends from an opening 144 in fluid passageway 32 to an intersection of fluid passageway 136. Fluid inlet openings 142 and 144 may particularly be circular and have a diameter in a range of 0.1 mm to 1 mm, which is narrower than the diameter of second passage 120.

With the foregoing construction, carbon dioxide sampling may be performed from either of inlet opening 142 in fluid passageway 120 or inlet opening 144 in fluid passageway 32. Thus, in the unlikely event on inlet becomes occluded, the remaining inlet may be used.

Figure 7:
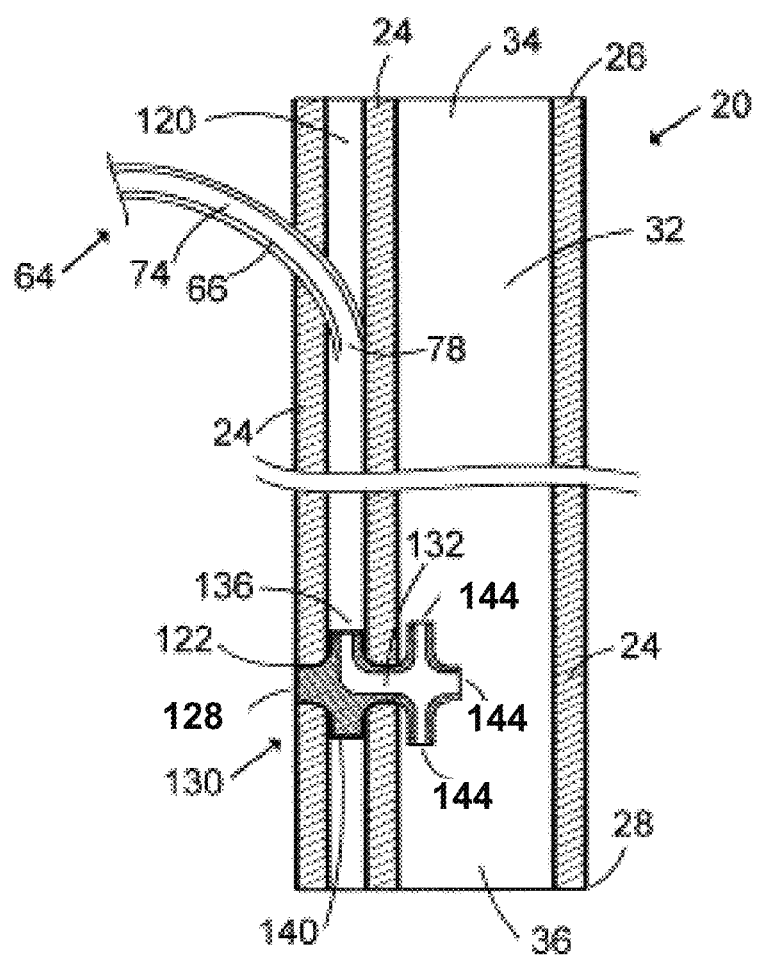
FIG. 7 shows a close-up sectional view of a distal end portion of another embodiment of an endotracheal tube apparatus according to the present disclosure.

In another embodiment of the present disclosure, as shown in FIG. 7, fluid sampling fitting 130 may include a plurality of fluid inlets 144 within first passageway 32.

Figures 8A, 8B, 8C:
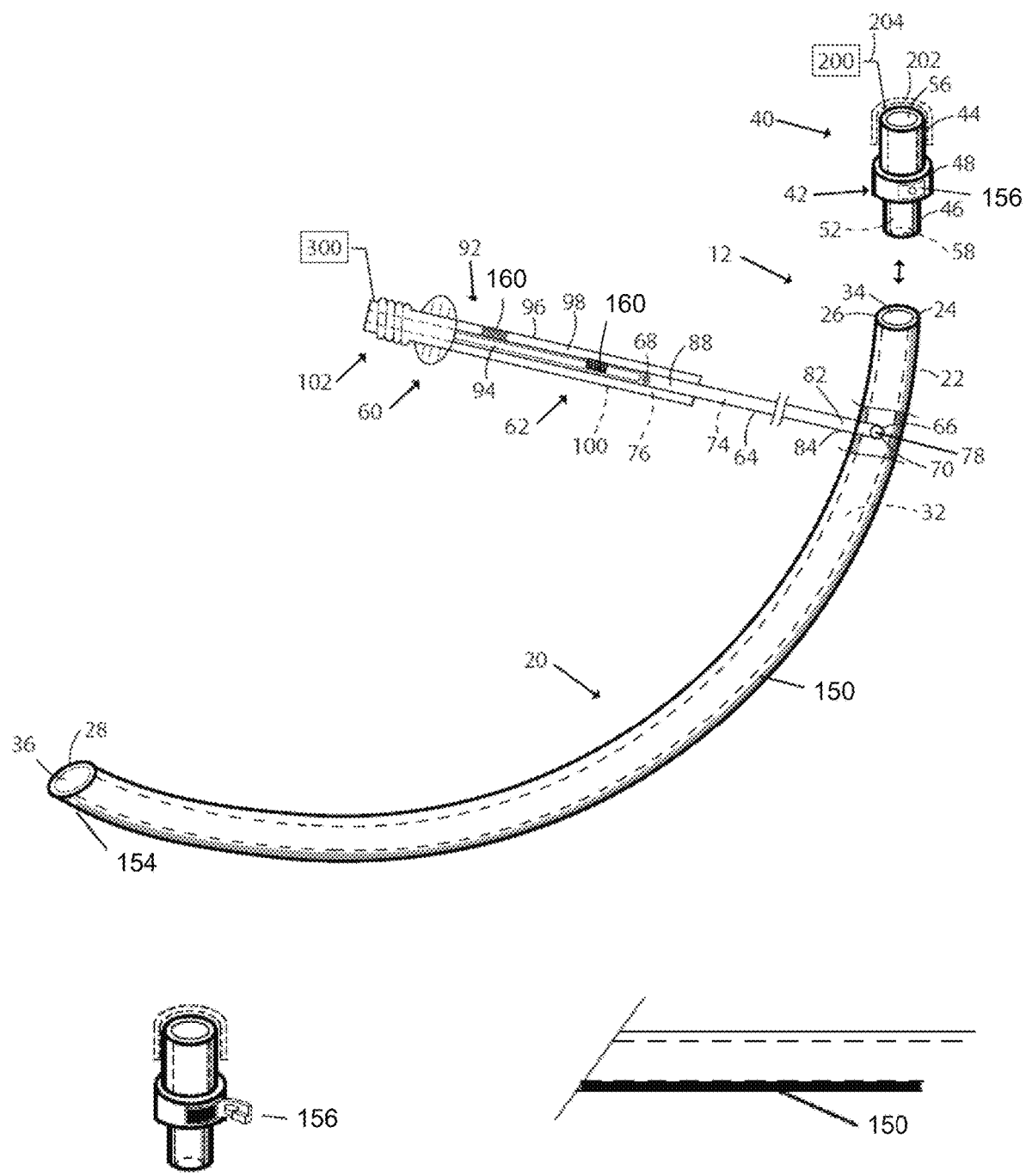
FIGS. 8A-8C show other embodiments of an endotracheal tube apparatus according to the present disclosure.

In other embodiments of the present disclosure, as shown in FIGS. 8A-8C, endotracheal tube 22 may include an elongated malleable member 150 which extends along a length of the endotracheal tube 22 from adjacent the proximal end 26 to adjacent the distal end 28. The elongated malleable member 150 may be used to conform the endotracheal tube 22 into various pre-determined shapes to be inserted into the patient. In certain embodiments, when made of metal, the elongated malleable member 150 may provide an electrical conductor in electrical communication with a light (LED) 154 adjacent the distal end 28 of the endotracheal tube 22. A proximal end of the electrical conductor may be in electrical communication with a power source 156 in the form of a battery locatable in adapter fitting 40. An exemplary metal member 150 may be obtained from Materion Corporation.

In certain embodiments, fluid sampling port 60 may include colorimetric paper 160 to detect a presence of carbon dioxide in the fluid sample exhaled from the patient. The colorimetric paper 160 (e.g. Kangaroo™ $CO_2$ colorimetric paper from Covidien) may be wrapped around filter 94 or otherwise be located within filter housing 96.

Figure 9:
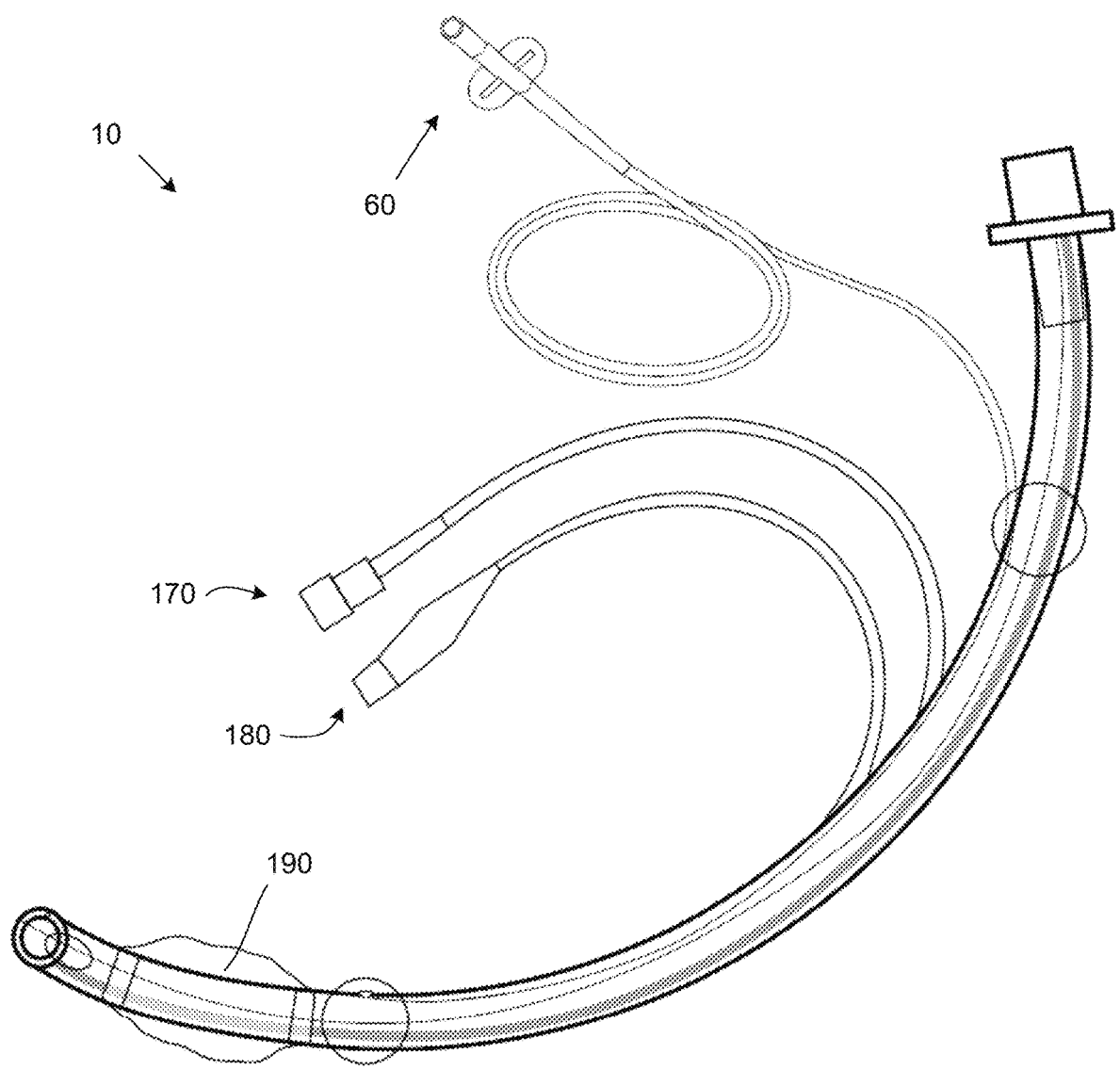
FIG. 9 shows another embodiment of an endotracheal tube apparatus according to the present disclosure.

In other embodiments of the present disclosure, as shown in FIG. 9, the endotracheal tube 22 may include a drug delivery port 170 and/or an inflation attachment port 180 in fluid communication with an inflation cuff 190.

Figure 10:
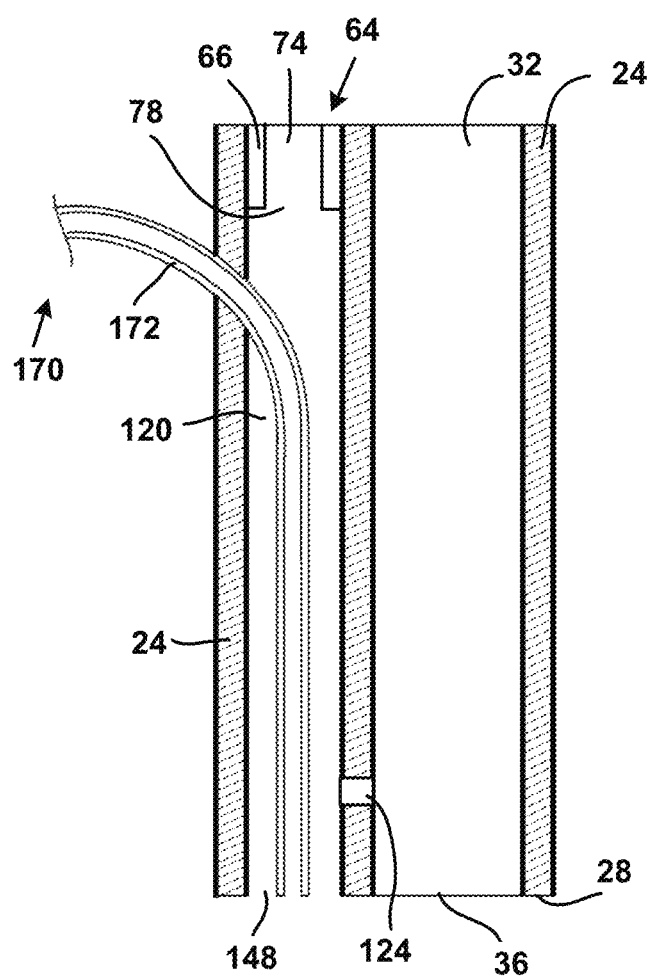
FIG. 10 shows a close-up sectional view of a distal end portion of another embodiment of an endotracheal tube apparatus according to the present disclosure.

In another embodiment of the present disclosure, as shown in FIG. 10, the drug delivery port 170 may comprise a circular drug delivery tube 172 (e.g. extruded tubing) having a smaller diameter than second passageway 120 which may pass through a portion of sidewall 24 and be inserted into and in fluid communication with second passageway 120, such as by a splice connection, similar to fluid sampling tube 64. As shown in FIG. 10, the distal end of the drug delivery tube 172 may extend adjacent the distal end 28 of endotracheal tube 22, however, it should be understood that the drug delivery tube 172 may terminate at any location within second passageway 120, particularly within about 25 mm of the distal end 28 of the endotracheal tube 22. In this manner, drugs may be delivered from aperture 148 at the distal end of second passageway 120 from drug delivery tube 172 within second passageway 120, and exhaled gases from the patient may also be collected through aperture 148 in the portion of passageway 120 surrounding the drug delivery tube 172.

In other embodiments, in the event aperture 148 may become clogged, a distal end portion of the sidewall 24 may include a circular aperture 124 (e.g. within 25 mm from the distal end 28 and, in certain embodiments within 10 mm from the distal end 28) which extends through an intermediate portion of side-wall 24 which defines both first fluid passageway 32 and second fluid passageway 120. In this manner, second fluid passageway 120 may be placed into fluid communication with first fluid passageway 132 within endotracheal tube 22. As shown, aperture 124 is formed transverse (perpendicular) to the longitudinal direction of endotracheal tube 22, as well as fluid passageway 32 and fluid passageway 120.

Figure 11:
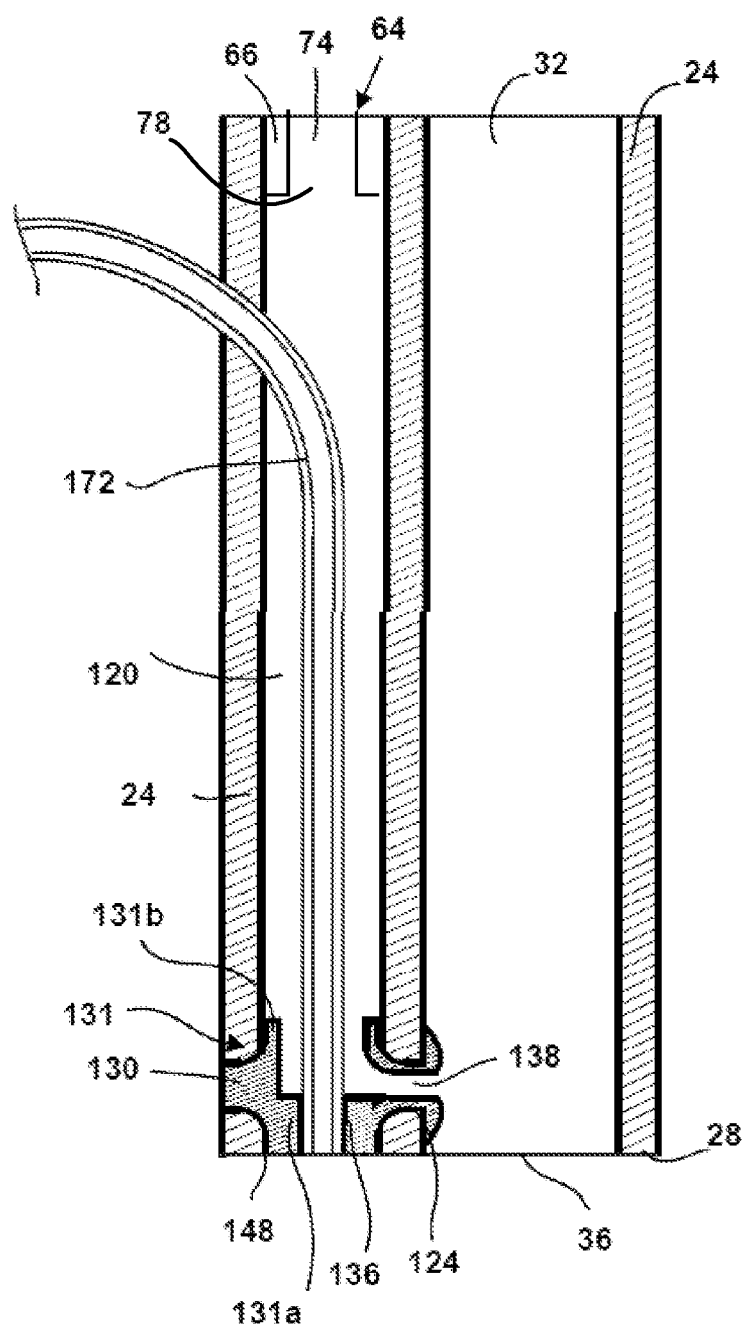
FIG. 11 shows a close-up sectional view of a distal end portion of another embodiment of an endotracheal tube apparatus according to the present disclosure.

In another embodiment, as shown in FIG. 11, the drug delivery tube 172 may pass through fluid passage 136 of fluid sampling fitting 130, which is shown in the form of a counterbore 131. The drug delivery tube 172 may seal with the distal portion 131a of the counterbore 131 by interference fit. As shown, the fluid passage 138 may be in fluid communication with the proximal portion 131b of the counterbore 131. In this manner, drug delivery and collection of exhaled gases may be performed at two separate locations remote from one another.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. An endotracheal tube apparatus having a proximal end and a distal end, and further comprising:
   an endotracheal tube having a proximal end and a distal end;
   a proximal end fitting having a proximal connector portion and a distal connector portion, the proximal end fitting located adjacent the proximal end of the endotracheal tube proximal to the proximal end of the endotracheal tube;
   a ventilation passageway disposed in the proximal end fitting and disposed in the endotracheal tube;
   wherein the proximal connector portion of the proximal end fitting provides the proximal end of the endotracheal tube apparatus;
   wherein the distal connector portion of the proximal end fitting is connected to the endotracheal tube;
   wherein the proximal end fitting includes a power source, wherein the power source comprises a battery, wherein the battery is located proximal to the proximal end of the endotracheal tube;
   wherein the battery is located in the proximal end fitting between the proximal connector portion and the distal connector portion;
   wherein the battery is configured to power at least one component of the endotracheal tube apparatus, wherein the at least one component comprises a light configured to emit light distal to the distal end of endotracheal tube, wherein the light is located adjacent the distal end of the endotracheal tube; and
   wherein, when the battery provides power to the light, the ventilation passageway within the proximal end fitting is open to a ventilation flow through the ventilation passageway.

2. The endotracheal tube apparatus of claim 1, wherein: the light comprises a light emitting diode.

3. The endotracheal tube apparatus of claim 1, wherein: the light is located in the endotracheal tube.

4. The endotracheal tube apparatus of claim 1, wherein: the endotracheal tube includes a conductor extending longitudinally to conduct energy along a longitudinal length of the endotracheal tube.

5. The endotracheal tube apparatus of claim 4, wherein: the conductor extends longitudinally from the proximal end fitting to a location adjacent the distal end of the endotracheal tube.

6. The endotracheal tube apparatus of claim 4, wherein: the conductor is an electrical conductor.

7. The endotracheal tube apparatus of claim 1, wherein: the proximal connector portion of the proximal end fitting is configured to be connected to a respirator tube.

8. The endotracheal tube apparatus of claim 1, wherein: at least one of the proximal connector portion and the distal connector portion is cylindrical.

9. The endotracheal tube apparatus of claim 1, wherein: the battery is located in a cavity of the proximal end fitting.

10. The endotracheal tube apparatus of claim 9, further comprising:
    a cover; and
    wherein the cavity is coverable by the cover.

11. The endotracheal tube apparatus of claim 1, wherein: the proximal connector portion and the distal connector portion are of a single body.

12. An endotracheal tube apparatus having a proximal end and a distal end, and further comprising:
    an endotracheal tube having a proximal end and a distal end;
    a proximal end fitting having a proximal connector portion and a distal connector portion, the proximal end fitting located adjacent the proximal end of the endotracheal tube proximal to the proximal end of the endotracheal tube;
    a ventilation passageway disposed in the proximal end fitting and disposed in the endotracheal tube;
    wherein the proximal connector portion of the proximal end fitting provides the proximal end of the endotracheal tube apparatus;

wherein the distal connector portion of the proximal end fitting is connected to the endotracheal tube;

wherein the proximal end fitting includes a power source, wherein the power source comprises a battery, wherein the battery is located proximal to the proximal end of the endotracheal tube;

wherein the battery is located in the proximal end fitting between the proximal connector portion and the distal connector portion;

wherein the battery is configured to power at least one component of the endotracheal tube apparatus, wherein the at least one component comprises a light configured to emit light distal to the distal end of endotracheal tube, wherein the light is located in the endotracheal tube; and wherein, when the battery provides power to the light, the ventilation passageway within the proximal end fitting is open to a ventilation flow through the ventilation passageway.

13. The endotracheal tube apparatus of claim 12, wherein: the light comprises a light emitting diode.

14. The endotracheal tube apparatus of claim 12, wherein: the light is located adjacent the distal end of the endotracheal tube.

15. The endotracheal tube apparatus of claim 12, wherein: the endotracheal tube includes a conductor extending longitudinally to conduct energy along a longitudinal length of the endotracheal tube.

16. The endotracheal tube apparatus of claim 15, wherein: the conductor is an electrical conductor.

17. The endotracheal tube apparatus of claim 15, wherein: the conductor extends longitudinally from the proximal end fitting to a location adjacent the distal end of the endotracheal tube.

18. The endotracheal tube apparatus of claim 12, wherein: the proximal connector portion of the proximal end fitting is configured to be connected to a respirator tube.

19. The endotracheal tube apparatus of claim 12, wherein: at least one of the proximal connector portion and the distal connector portion is cylindrical.

20. The endotracheal tube apparatus of claim 12, wherein: the battery is located in a cavity of the proximal end fitting.

21. The endotracheal tube apparatus of claim 20, further comprising:
a cover; and
wherein the cavity is coverable by the cover.

22. The endotracheal tube apparatus of claim 12, wherein: the proximal connector portion and the distal connector portion are of a single body.

* * * * *